United States Patent [19]

Holmwood et al.

[11] Patent Number: 4,999,440
[45] Date of Patent: Mar. 12, 1991

[54] FUNGICIDAL HYDROXYALKYL-TRIAZOLYL DERIVATIVES

[75] Inventors: Graham Holmwood, Wuppertal; Udo Kraatz, Leverkusen; Karl H. Büchel, Burscheid; Wilhelm Brandes, Leichlingen; Stefan Dutzmann, Duesseldorf; Paul Reinecke, Leverkusen, all of Fed. Rep. of Germany

[73] Assignee: Bayer Aktiengesellschaft, Leverkusen, Fed. Rep. of Germany

[21] Appl. No.: 395,233

[22] Filed: Aug. 17, 1989

Related U.S. Application Data

[62] Division of Ser. No. 190,733, May 5, 1988, Pat. No. 4,894,383.

[30] Foreign Application Priority Data

May 18, 1987 [DE] Fed. Rep. of Germany ....... 3716559

[51] Int. Cl.⁵ .................. C07D 303/12; C07D 303/08
[52] U.S. Cl. ..................... 549/556; 549/559; 548/267.8
[58] Field of Search ................. 549/559, 556; 548/262

[56] References Cited

U.S. PATENT DOCUMENTS 4,532,341 7/1985 Holmwood et al. ............... 549/559
4,797,499 1/1989 Holmwood et al. ............... 549/559

FOREIGN PATENT DOCUMENTS 3202602 8/1983 Fed. Rep. of Germany .

Primary Examiner—Richard L. Raymond
Assistant Examiner—Ba K. Trinh
Attorney, Agent, or Firm—Sprung, Horn, Kramer & Woods

[57] ABSTRACT

Fungicidal hydroxyalkyl-triazdyl derivatives of the formula

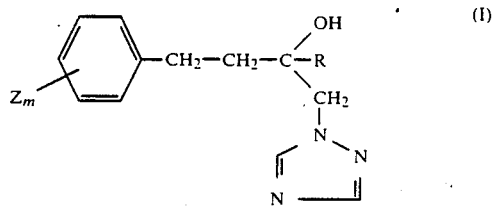

in which
R represents a radical of the formula $-CH_2-CH(CH_3)_2$, $-(CH_2)_4-CH_3$, $-(CH_2)_5-CH_3$, $-(CH_2)_6-CH_3$,

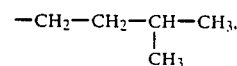

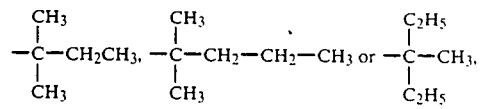

Z represents halogen, alkyl with 1 to 4 carbon atoms, halogenoalkyl with 1 or 2 carbon atoms and 1 to 5 halogen atoms, halogenoalkoxy with 1 or 2 carbon atoms and 1 to 5 halogen atoms, halogenoalkylthio with 1 or 2 carbon atoms and 1 to 5 halogen atoms, phenyl or alkoximinimethyl with 1 to 4 carbon atoms in the alkoxy group and
m represents the numbers 0, 1, 2 or 3, and addition products thereof with acids and metal salts. Intermediates of the formulas

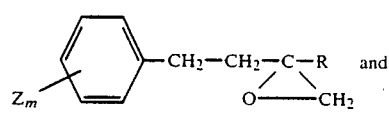

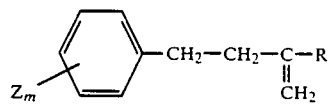

are also new.

2 Claims, 9 Drawing Sheets

FUNGICIDAL HYDROXYALKYL-TRIAZOLYL DERIVATIVES

This is a division of application Ser. No. 190,733, filed May 5, 1988, now U.S. Pat. No. 4,894,383.

The present invention relates to new hydroxyalkyl-triazolyl derivatives, a process for their preparation and their use as fungicides.

It has already been disclosed that numerous hydroxyalkyl-azolyl derivatives possess fungicidal properties (compare EP-OS (European Published Specification) No. 0,040,345 and EP-OS (European Published Specification) No. 0,061,835). Thus 1-(4-chlorophenyl)-4,4-dimethyl-3-(1,2,4-triazol-1-yl-methyl)pentan-3-ol, for example, is employed for combating fungi. The activity of this substance is very good; however, the plant tolerability and the activity in some cases leaves something to be desired.

New hydroxyalkyl-triazolyl derivatives of the formula

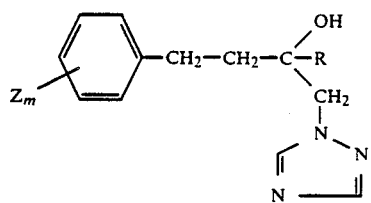

in which

R represents the radicals of the formulae —CH$_2$—CH(CH$_3$)$_2$, —(CH$_2$)$_4$—CH$_3$, —(CH$_2$)$_5$—CH$_3$, —(CH$_2$)$_6$—CH$_3$,

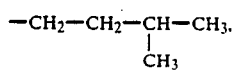

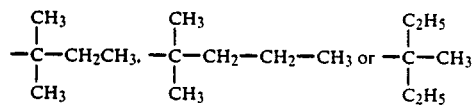

Z represents halogen, alkyl with 1 to 4 carbon atoms, halogenoalkyl with 1 or 2 carbon atoms and 1 to 5 halogen atoms, halogenoalkoxy with 1 or 2 carbon atoms and 1 to 5 halogen atoms, halogenoalkylthio with 1 or 2 carbon atoms and 1 to 5 halogen atoms, phenyl or alkoximinomethyl with 1 to 4 carbon atoms in the alkoxy group and m represents the numbers 0, 1, 2 or 3, and their acid addition salts and metal salt complexes, have been found.

The new hydroxyalkyl-triazolyl derivatives of the formula (I) possess an asymmetrically substituted carbon atom and can therefore exist in two optical isomeric forms. The invention relates both to the racemates and to the separate isomers and their mixtures.

Furthermore, it has been found that hydroxyalkyl-triazolyl derivatives of the formula (I) and their acid addition salts and metal salt complexes are obtained when oxiranes of the formula

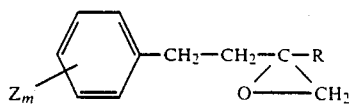

in which R, Z and m have the abovementioned meaning, are reacted with 1,2,4-triazole of the formula

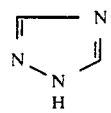

in the presence of a diluent and if appropriate in the presence of an acid binding agent and if appropriate in the presence of a catalyst and then if appropriate an acid or a metal salt is subsequently adducted to the compounds of the formula (I) so obtained.

Finally it has been found that the hydroxyalkyltriazolyl derivatives of the formula (I) and their acid addition salts and metal salt complexes are distinguished by very good fungicidal properties.

Surprisingly, the substances according to the invention possess a better fungicidal activity than 1-(4-chlorophenyl)-4,4-dimethyl-3-(1,2,4-triazol-1-yl-methyl)-pentan-3-ol, which is a constitutionally similar, previously known active substance with an equivalent type of action. In addition the substances according to the invention exhibit outstanding plant tolerability.

Formula (I) provides a general definition of the hydroxyalkyl-triazolyl derivatives according to the invention. Preferred compounds of the formula (I) are those in which R represents the radicals of the formulae —CH$_2$—CH(CH$_3$)$_2$, —(CH$_2$)$_4$—CH$_3$, —(CH$_2$)$_5$—CH$_3$, —(CH$_2$)$_6$—CH$_3$,

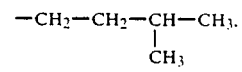

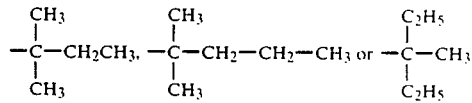

Z represents fluorine, chlorine, bromine, methyl, ethyl, trifluoromethyl, trifluoromethoxy, trifluoromethylthio, phenyl, methoximinomethyl or ethoximinomethyl and m represents the numbers 0, 1, 2 or 3.

When m represents 2 or 3, the substituents for Z can be identical or different.

Addition products of acids and those hydroxyalkyl-triazolyl derivatives of the formula (I), in which R, Z and m have those meanings which have already been mentioned as preferred for these substituents or this index in connection with the description of the substances according to the invention are also preferred compounds according to the invention.

The acids which can be added preferably include hydrohalic acids, such as, for example, hydrochloric acid and hydrobromic acid, in particular hydrochloric acid, furthermore to phosphoric acid, nitric acid, mono- and bi-functional carboxylic acids and hydroxycarboxylic acids, such as, for example, acetic acid, maleic acid, succinic acid, fumaric acid, tartaric acid, citric acid, salicylic acid, sorbic acid and lactic acid, and sulphonic acids, such as, for example, p-toluenesulphonic acid and 1,5-naphthalenedisulphonic acid.

Addition products of salts of metals of the main groups II to IV and the subgroups I and II and also IV to VIII of the periodic table of the elements and those hydroxyalkyl-triazolyl derivatives of the formula (I), in which R, Z and m have those meanings which have already been mentioned as preferred for these substituents or this index in connection with the description of the substances according to the invention are additionally preferred compounds according to the invention.

Herein, salts of copper, zinc, manganese, magnesium, tin, iron and nickel are particularly preferred. Possible anions of these salts are those which are derived from acids which lead to addition products which are physiologically tolerable for plants. In this connection, particularly preferred acids of this type are the hydrohalic acids, such as, for example, hydrochloric acid and hydrobromic acid, furthermore phosphoric acid, nitric acid and sulphuric acid.

Examples which may be mentioned for the compounds according to the invention are the substances shown in the following table.

TABLE

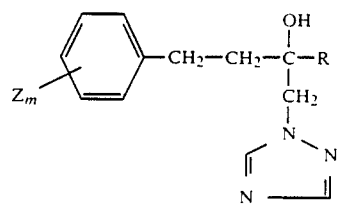

(I)

| $Z_m$ | R |
|---|---|
| 2,4-Cl$_2$ | —(CH$_2$)$_4$—CH$_3$ |
| 4-F | " |
| 4-CH=N—OCH$_3$ | " |
| 2,6-Cl$_2$ | " |
| 4-⟨phenyl⟩ | " |
| 4-CF$_3$ | " |
| 4-CH$_3$ | " |
| 2,4-Cl$_2$ | —(CH$_2$)$_5$—CH$_3$ |
| 4-F | " |
| 4-CH=N—OCH$_3$ | " |
| 2,6-Cl$_2$ | " |
| 4-⟨phenyl⟩ | " |
| — | " |
| 4-CF$_3$ | " |

TABLE-continued (I)

| $Z_m$ | R |
|---|---|
| 4-CH$_3$ | " |
| 2,4-Cl$_2$ | —(CH$_2$)$_6$—CH$_3$ |
| 4-F | " |
| 4-CH=N—OCH$_3$ | " |
| 2,6-Cl$_2$ | " |
| 4-⟨phenyl⟩ | " |
| — | " |
| 4-CF$_3$ | " |
| 4-CH$_3$ | " |
| 2,4-Cl$_2$ | —CH$_2$—CH$_2$—CH(CH$_3$)—CH$_3$ |
| 4-F | " |
| 4-CH=N—OCH$_3$ | " |
| 2,6-Cl$_2$ | " |
| 4-⟨phenyl⟩ | " |
| — | " |
| 4-CF$_3$ | " |
| 4-CH$_3$ | " |
| 2,4-Cl$_2$ | —C(CH$_3$)$_2$—CH$_2$—CH$_2$—CH$_3$ |
| 4-F | " |
| 4-CH=N—OCH$_3$ | " |
| 2,6-Cl$_2$ | " |
| 4-⟨phenyl⟩ | " |
| — | " |
| 4-CF$_3$ | " |
| 4-CH$_3$ | " |

If 2-[2-(4-chlorophenyl)-ethyl]-2-[(1,1-dimethyl)-butyl]-oxirane and 1,2,4-triazole are used as starting substances, then the course of the process according to invention can be represented by the following equation:

$$\text{Cl-} \langle \text{C}_6\text{H}_4 \rangle \text{-CH}_2\text{-CH}_2\text{-}\underset{\underset{\text{CH}_2}{|}}{\overset{\overset{}{|}}{\text{C}}}\text{-}\underset{\underset{\text{CH}_3}{|}}{\overset{\overset{\text{CH}_3}{|}}{\text{C}}}\text{-CH}_2\text{-CH}_2\text{-CH}_3 + \text{(1,2,4-triazole)} \xrightarrow{\text{Base}}$$

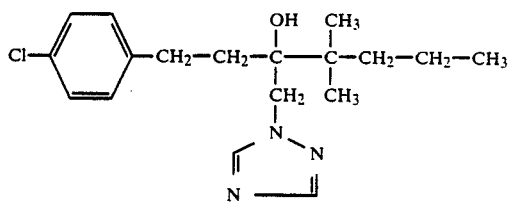

Formula (II) provides a general definition of the oxiranes to be used as starting substances in carrying out the process according to the invention. In this formula, R, Z and the index m preferably have those meanings which have already been mentioned as preferred for these substituents or for the index m in connection with the description of the substances of the formula (I) according to the invention.

The oxiranes of the formula (II) were hitherto unknown. They can be prepared by a process in which (a) in a first step, ketones of the formula

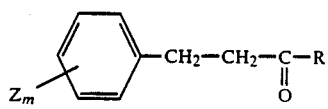
(IV)

in which

R, Z and m have the abovementioned meaning, are reacted with methyl-triphenyl-phosphonium bromide of the formula

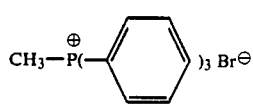
(V)

in the presence of a base and in the presence of a diluent and then in a second step the compounds so obtained of the formula

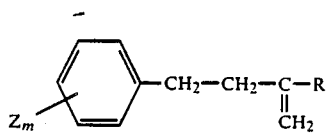
(VI)

in which

R, Z and m have the abovementioned meaning, with peracids in the presence of a diluent, or (b) ketones of the formula

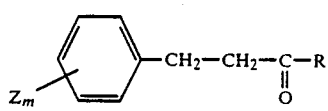
(IV)

in which

R, Z and m have the abovementioned meaning, are reacted either (α) with dimethyloxosulphonium methylide of the formula

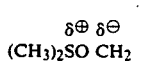
(VII)

or (β) with dimethylsulphonium methylide of the formula

(VIII)

in the presence of a diluent.

The ketones of the formula (IV) required as starting substances in the preparation of the oxiranes of the formula (II) are known or can be prepared in a simple manner by processes which are known in principle (compare EP-OS (European Published Specification) No. 0,084,834). Thus ketones of the formula (IV) are obtained by reacting compounds of the formula

(IX)

in which R' has the abovementioned meaning for R or represents corresponding unsaturated counterparts of R, with aldehydes of the formula

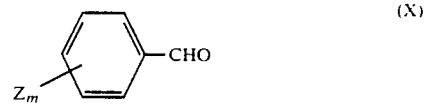
(X)

in which Z and m have the abovementioned meaning, in the presence of a diluent, such as, for example, ethanol, at temperatures between 0° and 60° C. and hydrogenating the compounds of the formula

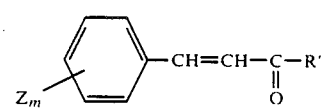
(XI)

in which R', Z and m have the abovementioned meaning, resulting in this reaction, using hydrogen in the presence of a catalyst, such as, for example, Raney nickel, in the presence of a diluent, such as, for example, toluene or tetrahydrofuran, at temperatures between 40° and 180° C. (compare the preparation examples).

The compounds of the formula (IX) and also the aldehydes of the formula (X) are known or can be prepared in a simple manner by known processes.

The methyl-triphenyl-phosphonium bromide of the formula (V) furthermore required as starting material in the preparation of the oxiranes of the formula (II) according to process (a) is known.

The compounds of the formula (VI) required in the second step as starting substances in the preparation of the oxiranes of the formula (II) according to the above process (a) were hitherto unknown.

In process (a) for the preparation of the oxiranes of the formula (II), the first step is carried out in the presence of a base. Possible bases here are all bases conventionally utilizable for Wittig reactions of this type. Potassium tert.-butylate is preferably utilizable.

In carrying out the first step of the above process (a) for the preparation of the oxiranes of the formula (II), suitable diluents are all organic solvents customary for such reactions. Aromatic hydrocarbons, such as benzene, toluene and xylene, are preferably utilizable.

In carrying out the second step of the above process (a) for the preparation of the oxiranes of the formula (II), possible reagents for epoxidation are all the customary peracids. Meta-chloroperbenzoic acid and peracetic acid are preferably utilizable. In addition, it is also possible to employ a mixture of acetic acid and hydrogen peroxide.

In carrying out the second step of the above process (a) for the preparation of the oxiranes of the formula (II), suitable diluents are all the solvents customary for such epoxidations. Dichloromethane, chloroform, toluene, dichlorobenzene, acetic acid and other inert solvents are preferably utilizable.

In carrying out process (a) for the preparation of the oxiranes of the formula (II), the reaction temperatures can be varied within a certain range. In general the first step is carried out at temperatures between 50° C. and 140° C., preferably between 80° C. and 120° C. The second step is generally carried out between 10° C. and 60° C., preferably between 20° C. and 50° C.

In carrying out the process (a) for the preparation of the oxiranes of the formula (II), a procedure is generally followed in which between 1 and 3 mols of methyltriphenylphosphonium bromide of the formula (V) and between 1 and 3 mols of base are employed per mol of ketone of the formula (IV) in the first step. In the second step, between 1 and 2 mols of peracid are in each case employed per mol of a compound of the formula (VI). In each case, working up is according to customary methods.

The dimethyloxosulphonium methylide of the formula (VII) required as reaction component in process (b) is known (compare J. Amer. Chem. Soc. 87, 1363–1364 (1965)). It is used in the above reaction in the freshly prepared state, in that it is obtained in situ by reaction of trimethyloxo-sulphonium iodide with sodium hydride or sodium amide, in particular with potassium tert.-butylate or sodium methylate, in the presence of a diluent.

The dimethylsulphonium methylide of the formula (VIII) additionally possible as a reaction component in process (b) is also known (compare Heterocycles 8, 397 (1977)). It is also employed in a freshly prepared state in the above reaction, in that it is obtained in situ, for example, from trimethylsulphonium halide or trimethylsulphonium methyl sulphate, in the presence of a strong base, such as, for example, sodium hydride, sodium amide, sodium methylate, potassium tert.-butylate or potassium hydroxide, in the presence of a diluent, such as tert.-butanol or dimethyl sulphoxide.

In carrying out process (b), suitable diluents are inert organic solvents. Alcohols, such as tert.-butanol, ethers, such as tetrahydrofuran or dioxane, furthermore aliphatic and aromatic hydrocarbons, such as benzene, toluene or xylene, and also strongly polar solvents, such as dimethyl sulphoxide, are preferably utilizable.

The reaction temperatures can be varied within a relatively wide range in process (b). In general, the reaction is carried out at temperatures between 0° and 100° C., preferably between 10° and 60° C.

In carrying out process (b), 1 to 3 mols of dimethyloxosulphonium methylide of the formula (VII) or dimethylsulphonium methylide of the formula (VIII) are preferably employed per mol of ketone of the formula (IV). The isolation of the oxiranes is according to customary methods.

In the process according to the invention, the oxiranes of the formula (II) can, if appropriate, be directly reacted further without isolation.

Suitable diluents for the process according to the invention are organic solvents which are inert under the reaction conditions. Alcohols, such as, for example, ethanol, methoxyethanol or propanol; ketones, such as, for example, 2-butanone and n-methylpyrrolidone; nitriles, such as, for example, acetonitrile; esters, such as, for example, ethyl acetate; ethers, such as, for example, dioxane; aromatic hydrocarbons, such as, for example, benzene and toluene; or amides, such as, for example, dimethylformamide, are preferably utilizable.

Possible bases for the process according to the invention are all the conventionally utilizable inorganic and organic bases. Alkali metal carbonates, such as, for example, sodium carbonate and potassium carbonate; alkali metal hydroxides, such as, for example, sodium hydroxide; alkali metal alcoholates, such as, for example, sodium methylate and potassium methylate, and sodium ethylate and potassium ethylate; alkali metal hydrides, such as, for example, sodium hydride; and also lower tertiary alkylamines, cycloalkylamines and aralkylamines, such as triethylamine in particular, are preferably utilizable.

In carrying out the process according to the invention, suitable catalysts are all the reaction accelerators conventionally employable for such reactions. α,α'-Azo-isobutyronitrile is preferably utilizable.

In carrying out the process according to the invention, the reaction temperatures can be varied within a relatively wide range. In general, the reaction is carried out at temperatures between 0° and 200° C., preferably between 60° and 150° C.

In carrying out the process according to the invention, the reaction is generally carried out under atmospheric pressure. However, it is also possible to work under increased or reduced pressure.

In carrying out the process according to the invention, 1 to 2 mols of 1,2,4-triazole and, if appropriate, 1 to 2 mols of an acid binding agent are preferably employed per mol of oxirane of the formula (II). Working up and isolation of the final products are according to customary methods.

The compounds of the formula (I) obtainable by the processes according to the invention can be converted into acid addition salts or metal salt complexes.

Suitable acids for the preparation of acid addition salts of the compounds of the formula (I) are preferably those acids which have already been mentioned as preferred acids in connection with the description of the acid addition salts according to the invention.

The acid addition salts of the compounds of the formula (I) can be obtained in a simple manner by customary salt formation methods, for example by dissolving a compound of the general formula (I) in a suitable inert solvent and adding the acid, for example, hydrochloric acid, and can be isolated in a known manner, for example by filtering off, and purified, if necessary, by washing with an inert organic solvent.

For the preparation of metal salt complexes of the compounds of the general formula (I), suitable salts of metals are preferably those which have already been described above.

The metal salt complexes of compounds of the general formula (I) can be obtained in a simple manner by customary processes, for example, by dissolving the metal salt in alcohol, for example ethanol, and adding to compounds of the general formula (I). Metal salt complexes can be isolated in a known manner, for example by filtering off, and purified, if necessary, by recrystallization.

The active compounds according to the invention exhibit a strong microbicidal action and can be employed as fungicides.

Fungicidal agents in plant protection are employed for combating Plasmodiophoromycetes, Oomycetes, Chytridiomycetes, Zygomycetes, Ascomycetes, Basidiomycetes and Deuteromycetes.

Some causative organisms of fungal and bacterial diseases which come under the generic names listed above may be mentioned as examples, but not by way of limitation: Xanthomonas species, such as *Xanthomonas oryzae*; Pseudomonas species, such as *Pseudomonas lachrymans*; Erwinia species, such as *Erwinia amylovora*; Pythium species, such as *Pythium ultimum*; Phytophthora species, such as *Phytophthora infestans*; Pseudoperonospora species, such as *Pseudoperonospora humuli* or *Pseudoperonospora cubense*; Plasmopara species, such as *Plasmopara viticola*; Peronospora species, such as *Peronospora pisi* or *P. brassicae*; Erysiphe species, such as *Erysiphe graminis*; Sphaerotheca species, such as *Sphaerotheca fuliginea*; Podosphaera species, such as *Podosphaera leucotricha*; Venturia species, such as *Venturia inaequalis*; Pyrenophora species, such as *Pyrenophora teres* or *P. graminea* (conidia form: Drechslera, syn: Helminthosporium); Cochliobolus species, such as *Cochliobolus sativus* (conidia form: Drechslera, syn: Helminthosporium); Uromyces species, such as *Uromyces appendiculatus*; Puccinia species, such as *Puccinia recondita*; Tilletia species, such as *Tilletia caries*; Ustilago species, such as *Ustilago nuda* or *Ustilago avenae*; Pellicularia species, such as *Pellicularia sasakii*; Pyricularia species, such as *Pyricularia oryzae*; Fusarium species, such as *Fusarium culmorum*; Botrytis species, such as *Botrytis cinerea*; Septoria species, such as *Septoria nodorum*; Leptosphaeria species, such as *Leptosphaeria nodorum*; Cercospora species, such as *Cercospora canescens*; Alternaria species, such as *Alternaria brassicae* and Pseudocercosporella species, such as *Pseudocercosporella herpotrichoides*.

The good toleration, by plants, of the active compounds, at the concentrations required for combating plant diseases, permits treatment of above-ground parts of plants, of vegetative propagation stock and seeds, and of the soil.

The substances according to the invention can be employed with particularly good effect as plant protection agents for combating Venturia (apple), Cercospora (mungo bean) and also Erysiphe, Puccinia, Leptosphaeria, Cochliobolus and Pyrenophora in cereals and Pyricularia and Pellicularia in rice.

Moreover, the compounds according to the invention possess a good, wide spectrum of action in vitro.

The active compounds can be converted into the customary formulations, such as solutions, emulsions, suspensions, powders, foams, pastes, granules, aerosols, very fine capsules in polymeric substances and in coating compositions for seed, as well as ULV formulations.

These formulations are produced in a known manner, for example by mixing the active compounds with extenders, that is, liquid solvents, liquefied gases under pressure, and/or solid carriers, optionally with the use of surface-active agents, that is, emulsifying agents and/or dispersing agents, and/or foam-forming agents. In the case of the use of water as an extender, organic solvents can, for example, also be used as auxiliary solvents. As liquid solvents, there are suitable in the main: aromatics, such as xylene, toluene or alkyl naphthalenes, chlorinated aromatics or chlorinated aliphatic hydrocarbons, such as chlorobenzenes, chloroethylenes or methylene chloride, aliphatic hydrocarbons, such as cyclohexane or paraffins, for example mineral oil fractions, alcohols, such as butanol or glycol as well as their ethers and esters, ketones, such as acetone, methyl ethyl ketone, methyl isobutyl ketone or cyclohexanone, strongly polar solvents, such as dimethylformamide and dimethylsulphoxide, as well as water. By liquefied gaseous extenders or carriers are meant liquids which are gaseous at normal temperature and under normal pressure, for example aerosol propellants, such as halogenated hydrocarbons as well as butane, propane, nitrogen and carbon dioxide. As solid carriers there are suitable: for example, ground natural minerals, such as kaolins, clays, talc, chalk, quartz, attapulgite, montmorillonite or diatomaceous earth, and ground synthetic minerals, such as highly-dispersed silicic acid, alumina and silicates. As solid carriers for granules there are suitable: for example, crushed and fractionated natural rocks such as calcite, marble, pumice, sepiolite and dolomite, as well as synthetic granules of inorganic and organic meals, and granules of organic material such as sawdust, coconut shells, corn cobs and tobacco stalks. As emulsifying and/or foam-forming agents there are suitable: for example, non-ionic and anionic emulsifiers, such as polyoxyethylene-fatty acid esters, polyoxyethylene-fatty alcohol ethers, for example alkylaryl polyglycol ethers, alkylsulphonates, alkyl-sulphates, arylsulphonates as well as albumin hydrolysis products. As dispersing agents there are suitable: for example, ligninsulphite waste liquors and methylcellulose.

Adhesives such as carboxymethylcellulose and natural and synthetic polymers in the form of powders, granules or latices, such as gum arabic, polyvinyl alcohol and polyvinyl acetate, as well as natural phospholipids, such as cephalins and lecithins, and synthetic phospholipids, can be used in the formulations. Further additives can be mineral and vegetable oils.

It is possible to use colorants such as inorganic pigments, for example iron oxide, titanium oxide and Prussian Blue, and organic dyestuffs, such as alizarin dyestuffs, azo dyestuffs and metal phthalocyanine dyestuffs, and trace nutrients such as salts of iron, manganese, boron, copper, cobalt, molybdenum and zinc.

The formulations in general contain between 0.1 and 95 per cent by weight of active compound, preferably between 0.5 and 90%.

The active compounds according to the invention can be present in the formulations as a mixture with other known active compounds, such as fungicides, insecticides, acaricides and herbicides, and also as mixtures with fertilizers and other growth regulators.

The active compounds can be used as such, in the form of their formulations or as the use forms prepared therefrom, such as ready-to-use solutions, emulsifiable concentrates, emulsions, foams, suspensions, wettable powders, pastes, soluble powders, dusting agents and granules. They are used in the customary manner, for example by watering, spraying, atomizing, scattering, dusting, foaming, coating and the like. Furthermore, it is possible to apply the active compounds in accordance with the ultra-low volume process or to inject the active compound preparation or the active compound itself into the soil. It is also possible to treat the seeds of the plants.

When the compounds according to the invention are used as fungicides the amount applied can be varied within a substantial range depending upon the type of application. Thus the active compound concentrations in the use forms in the treatment of parts of plants are generally between 1 and 0.0001% by weight, preferably between 0.5 and 0.001%. In the treatment of seeds, in general amounts of active compounds of 0.001 to 50 g for each kilogram of seed, preferably 0.01 to 10 g, are required. In the treatment of soil, active compound concentrations of 0.00001 to 0.1% by weight, preferably 0.0001 to 0.02%, are necessary at the place of action.

The preparation and the use of the compounds according to the invention can be seen from the following examples.

PREPARATION EXAMPLES

Example 1

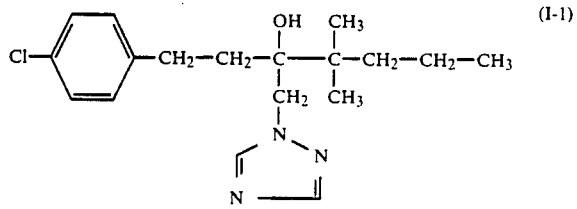
(I-1)

A solution of 20.5 g (0.077 mol) of 2-(4-chlorophenylethyl)-2-(1,1-dimethylbutyl)-oxirane, 5.3 g (0.077 mol) of 1,2,4-triazole, 1.0 g (0.025 mol) of sodium hydroxide, 1 ml of water and a spatula tipful of α,α'-azoisobutyronitrile in 50 ml of N-methylpyrrolidone is heated at 120° C. for 5 hours. After this, the solution is cooled to room temperature and concentrated by stripping off the solvent under reduced pressure, the remaining residue is dissolved in acetic acid and washed three times with water, the organic phase is dried over sodium sulphate and the solvent is removed under reduced pressure. The residue is purified by column chromatography (silica gel; dichloromethane:ethyl acetate=4:1). In this manner 16.0 g (61.9% of theory) of 1-(4-chlorophenyl)-4,4-dimethyl-3-(1,2,4-triazol-1-yl-methyl)-3-heptanol are obtained in the form of a yellow oil.

Preparation of starting products

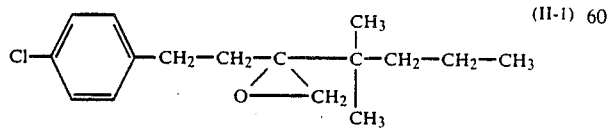
(II-1)

A solution of 18.2 g (0.106 mol) of m-chloroperbenzoic acid in 250 ml of dichloromethane is added dropwise to a boiling solution of 22 g (0.88 mol) of 2-(4-chlorophenylethyl)-3,3-dimethyl-1-hexene in 100 ml of dichloromethane during the course of 2.5 hours. The mixture is heated for a further 2 hours under reflux, then cooled to room temperature, initially washed three times with 1N aqueous sodium hydroxide solution and thereafter with water, and the organic phase is then dried over sodium sulphate and concentrated by stripping off the solvent under reduced pressure. 20.5 g of a colourless oil, which according to gas chromatographic and mass spectrometric analysis consists to 89.6% of 2-(4-chlorophenylethyl)-2-(1,1-dimethylbutyl)-oxirane, are obtained. Accordingly, the yield is calculated as 78.5% of theory. The product is used for the further reaction without additional purification.

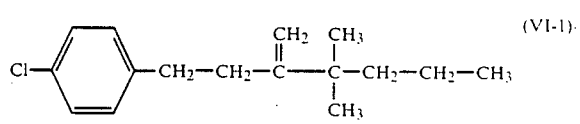
(VI-1)

A suspension of 47.4 g (0.133 mol) of methyl-triphenylphosphonium bromide and 15.3 g (0.137 mol) of potassium tert.-butylate in 250 ml of absolute toluene is heated under reflux for 30 minutes under dry nitrogen. 25.3 g (0.1 mol) of 1-(4-chlorophenyl)-4,4-dimethyl-3-heptanone, dissolved in 10 ml of absolute toluene, are then added dropwise during the course of 5 minutes. The reaction mixture is heated under reflux for a further 15 hours, then cooled to room temperature, washed twice with water and concentrated under reduced pressure. The residue is taken up in ethyl acetate, cooled to 5° C. and the crop of crystals formed is filtered off by suction. The filtrate is concentrated and distilled under reduced pressure. 23 g (91.8% of theory) of 2-(4-chlorophenylethyl)-3,3-dimethyl-1-hexene are obtained in the form of a yellow oil of boiling point 85°-87° C./0.1 mbar.

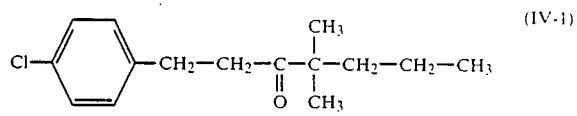
(IV-1)

15 g of Raney nickel are added to a solution of 92 g (0.37 mol) of 1-(4-chlorophenyl)-4,4-dimethyl-1,6-heptadien-3-one in 400 ml of tetrahydrofuran and the mixture is stirred for 2.5 hours at 40° C. under a hydrogen pressure of 50 bar in an autoclave. After this, the reaction mixture is filtered and concentrated under reduced pressure. After distillation of the residue in vacuo, 55 g (58.9% of theory) of 1-(4-chlorophenyl)-4,4-dimethyl-3-heptanone are obtained in the form of a yellow oil of boiling point 179° C./16 mbar.

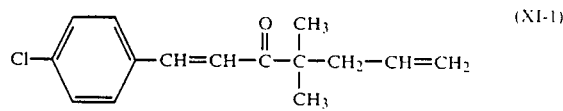
(XI-1)

40 ml of water are added to a solution of 56.2 g (0.4 mol) of 4-chlorobenzaldehyde and 50.4 g (0.4 mol) of 4,4-dimethyl-1-hexen-5-one in 200 ml of ethanol and directly thereafter a solution of 1.2 g of sodium hydroxide in 12 ml of water is added. The mixture is initially stirred for 1 hour at room temperature, then 0.8 g of solid sodium hydroxide is added and the mixture is stirred for a further 16 hours. It is then diluted with water and extracted with ethyl acetate. The ethyl acetate extract is washed three times with water, dried and concentrated. 92 g (92.5% of theory) of 1-(4-chlorophenyl)-4,4-dimethyl-1,6-heptadien-3-one are obtained in the form of a yellow oil.

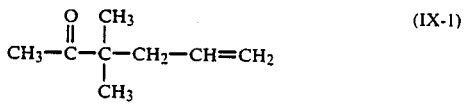
(IX-1)

A mixture of 121 g (1.0 mol) of 3-bromopropene and 103 g (1.2 mol) of 3-methyl-2-butanone is added dropwise during the course of 2 hours to a suspension of 168 g (3.0 mol) of potassium hydroxide powder and 10 g of tetrabutylammonium bromide in 300 ml of toluene with stirring. During this addition, the reaction temperature is kept below 30° C. The reaction mixture is kept at room temperature for a further 2 hours, then mixed with water, and the organic phase is separated. The organic phase is washed twice with water, dried and distilled through a packed column at ambient pressure. 40 g (31.7% of theory) of 4,4-dimethyl-1-hexen-5-one are obtained as a clear liquid of boiling point 151°-154° C.

Example 2

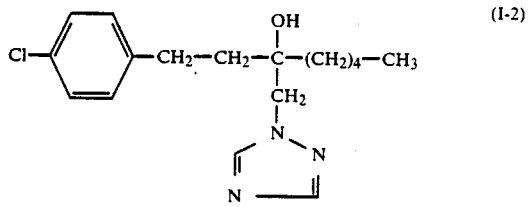
(I-2)

A solution of 89 g (0.352 mol) of 2-(4-chlorophenylethyl)-2-pentyl-oxirane, 26.5 g (0.384 mol) of 1,2,4-triazole, 3.5 g (0.0875 mol) of sodium hydroxide, 1.2 ml of water and a spatula tipful of α,α'-azoisobutyronitrile in 175 ml of N-methylpyrrolidone is heated at 120° C. for 4 hours. After this the mixture is cooled to room temperature and concentrated by stripping off the solvent under reduced pressure, the remaining residue is dissolved in ethyl acetate and washed three times with water, the organic phase is dried over sodium sulphate and the solvent is removed under reduced pressure. The residue is purified by column chromatography (silica gel; dichloromethane:ethyl acetate=1:1). In this manner 53.2 g (47.0% of theory) of 1-(4-chlorophenyl)-3-(1,2,4-triazol-1-yl-methyl)-3-octanol are obtained in the form of a yellow oil.

Preparation of starting products

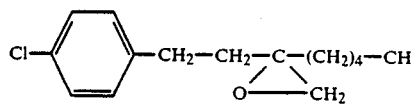
(II-2)

38 ml (0.61 mol) of iodomethane are added dropwise to a cooled solution of 47.6 ml (0.65 mol) of dimethyl sulphide in 280 ml of absolute dimethyl sulphoxide and 150 ml of absolute tetrahydrofuran. The mixture is stirred at room temperature for 16 hours. A solution of 97.5 g (0.41 mol) of 1-(4-chlorophenyl)-3-octanone in 400 ml of absolute toluene is added, the reaction mixture is cooled to 0°-5° C. and 41 g (0.76 mol) of sodium methylate are added in portions in the course of 3 hours. The mixture is stirred for a further 15 hours at room temperature, then 1 l of water is added, the organic phase is separated off and the aqueous phase is extracted once with toluene. The combined organic phases are washed twice with plenty of water, dried over sodium sulphate and concentrated by stripping off the solvent under reduced pressure. 93.2 g of a colorless oil which, according to gas chromatographic and mass spectrometric analysis consists to 84.5% of 2-(4-chlorophenylethyl)-2-pentyloxirane, are obtained. Accordingly, the yield is calculated as 76.1% of theory. The product is used for the further reaction without additional purification.

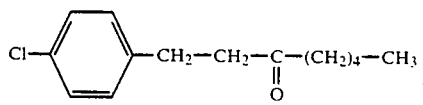
(IV-2)

15 g of Raney nickel are added to a solution of 100 g (0.423 mol) of 1-(4-chlorophenyl)-1-octen-3-one in 500 ml of toluene and the mixture is stirred for 5 hours at 60° C. under a hydrogen pressure of 70-90 bar in an autoclave. After this the reaction mixture is filtered and concentrated under reduced pressure. 97.3 g (96.4% of theory) of 1-(4-chlorophenyl)-3-octanone are obtained in the form of a colorless oil.

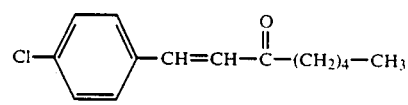
(XI-2)

70 ml of water are added to a solution of 90 g (0.64 mol) of 4-chlorobenzaldehyde and 68.5 g (0.6 mol) of 2-heptanone in 300 ml of ethanol and directly thereafter a solution of 1.7 g of sodium hydroxide in 17 ml of water is added. The mixture is initially stirred for 1 hour at room temperature, then 0.6 g of solid sodium hydroxide is added and the mixture is stirred for a further 64 hours. The precipitated product is filtered off with suction, washed with 1 liter of water, pressed out on a clay plate and then dried in vacuo for 16 hours over phosphorus pentoxide. 135 g (95.1% of theory) of 1-(4-chlorophenyl)-1-octen-3-one are obtained in the form of a pale yellow solid of melting point 44°-47° C.

The compounds shown in the following table by formula are also prepared according to the method given in Example 2.

TABLE

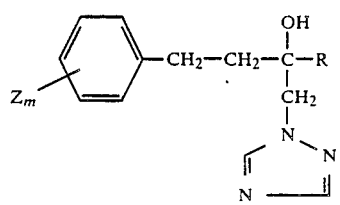

| Example | Compound No. | $Z_m$ | R | Characterization by |
|---|---|---|---|---|
| 3 | (I-3) | 4-Cl | —(CH₂)₅—CH₃ | NMR spectrum |
| 4 | (I-4) | 4-Cl | —(CH₂)₆—CH₃ | NMR spectrum |
| 5 | (I-5) | 4-Cl | —CH₂—CH₂—CH(CH₃)₂ | Melting point 78–79° C. |
| 6 | (I-6) | 4-CH=NOCH₃ | —CH₂—CH(CH₃)₂ | NMR spectrum |
| 7 | (I-7) | 4-CH=NOCH₃ | —CH₂—CH₂—CH(CH₃)₂ | NMR spectrum |
| 8 | (I-8) | 4-Cl | —CH₂—CH(CH₃)₂ | NMR spectrum |
| 9 | (I-9) | 4-Cl | —C(C₂H₅)(CH₃)(C₂H₅) | Melting point 112–113° C. |
| 10 | I-10 | 4-F | —C(CH₃)(CH₂CH₂CH₃)(CH₃) | Melting point 52–55° C. |
| 11 | I-11 | 4-F | —C(C₂H₅)(CH₃)(C₂H₅) | Melting point 83–84° C. |
| 12 | I-12 | — | —C(CH₃)(CH₂CH₂CH₃)(CH₃) | Melting point 84.5° C. |
| 13 | I-13 | 4-OCF₃ | —C(CH₃)(CH₂—CH₂—CH₃)(CH₃) | NMR spectrum |
| 14 | I-14 | 4-CH₃ | —C(CH₃)(CH₂CH₂CH₃)(CH₃) | NMR spectrum |

Figure 1:
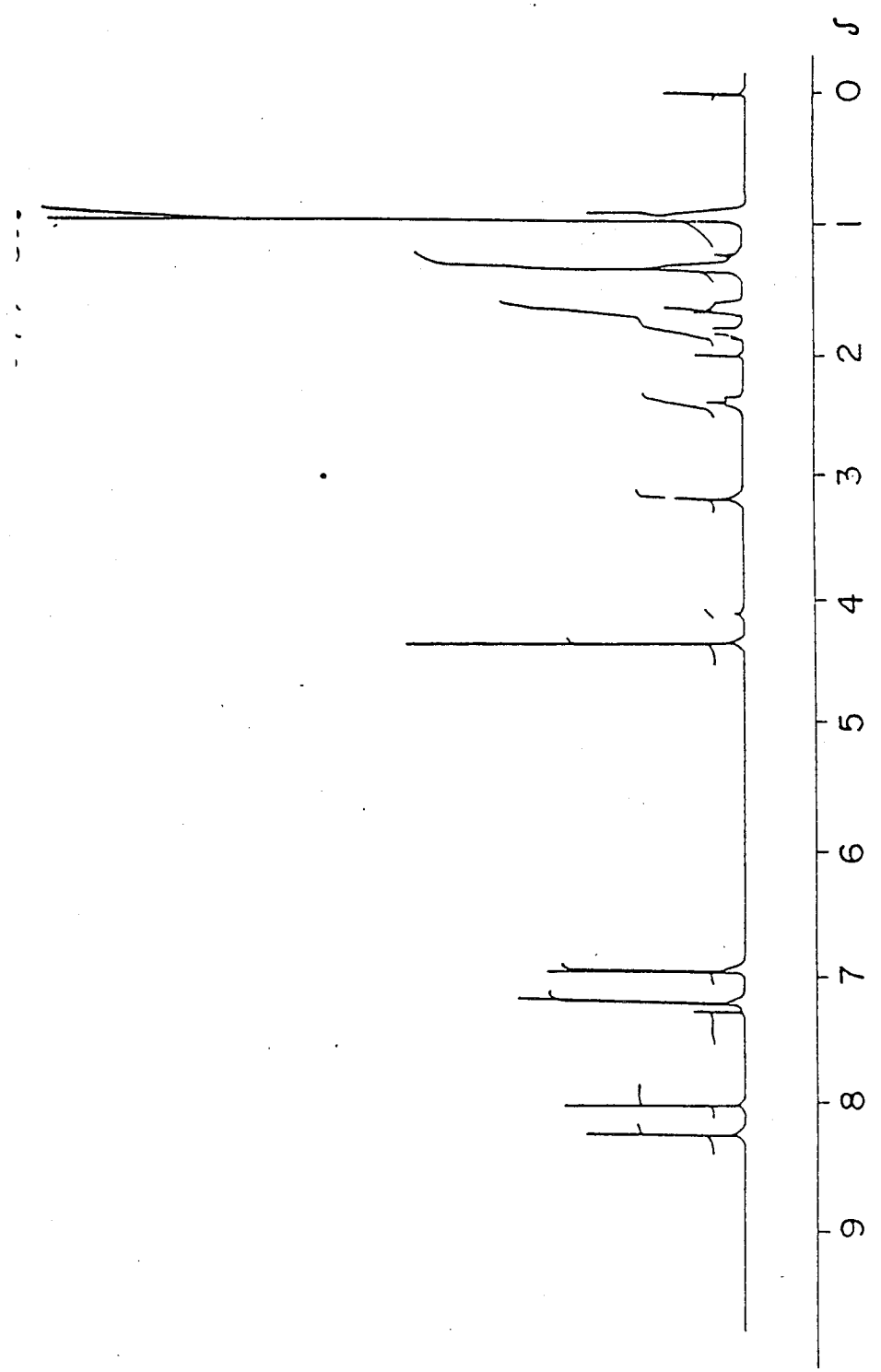
FIG. 1 represents the nuclear magnetic resonance spectrum characteristic of the compound prepared in Example 1.
Figure 2:
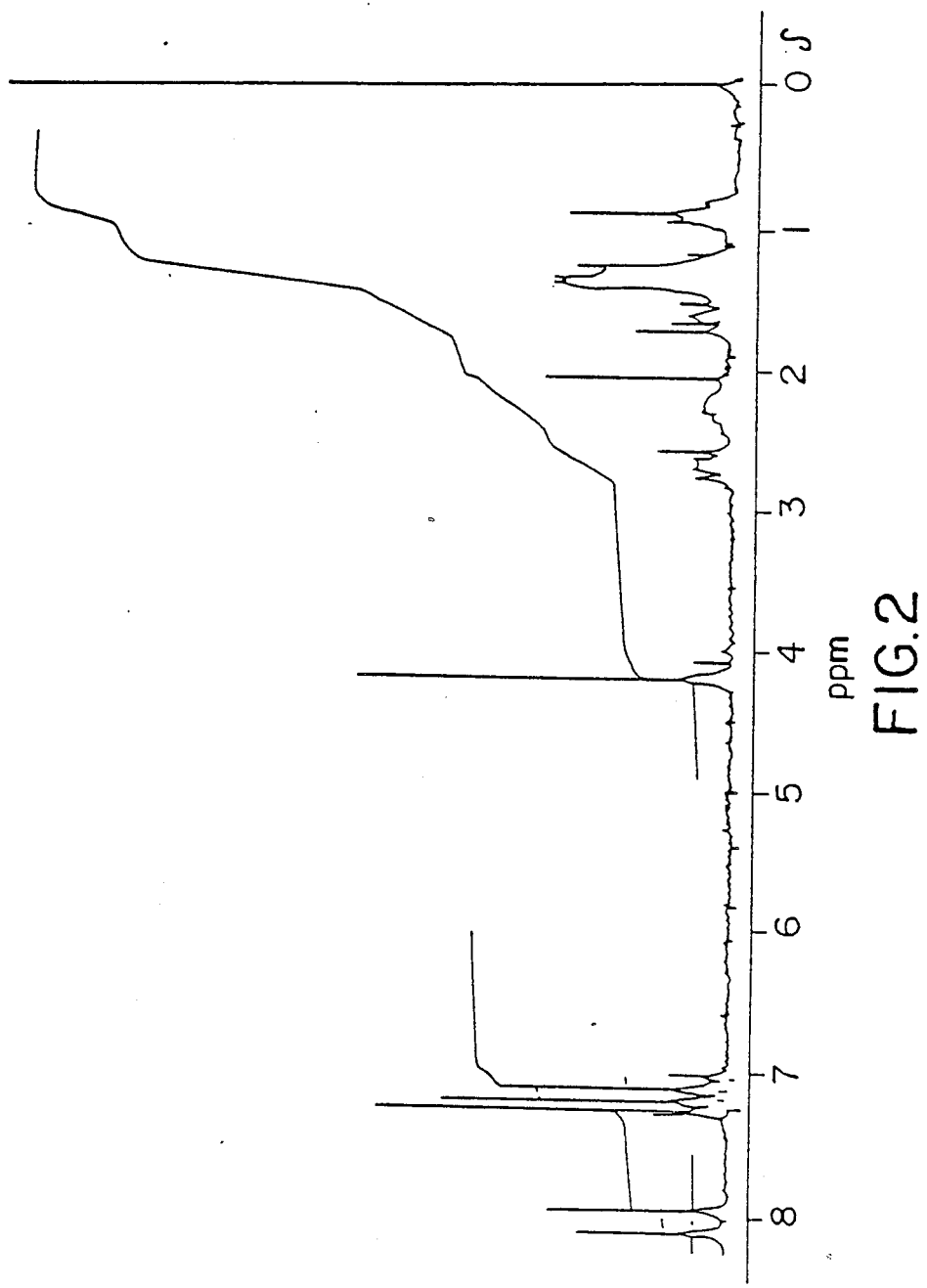
FIG. 2 represents the nuclear magnetic resonance spectrum characteristic of the compound prepared in Example 2.
Figure 3:
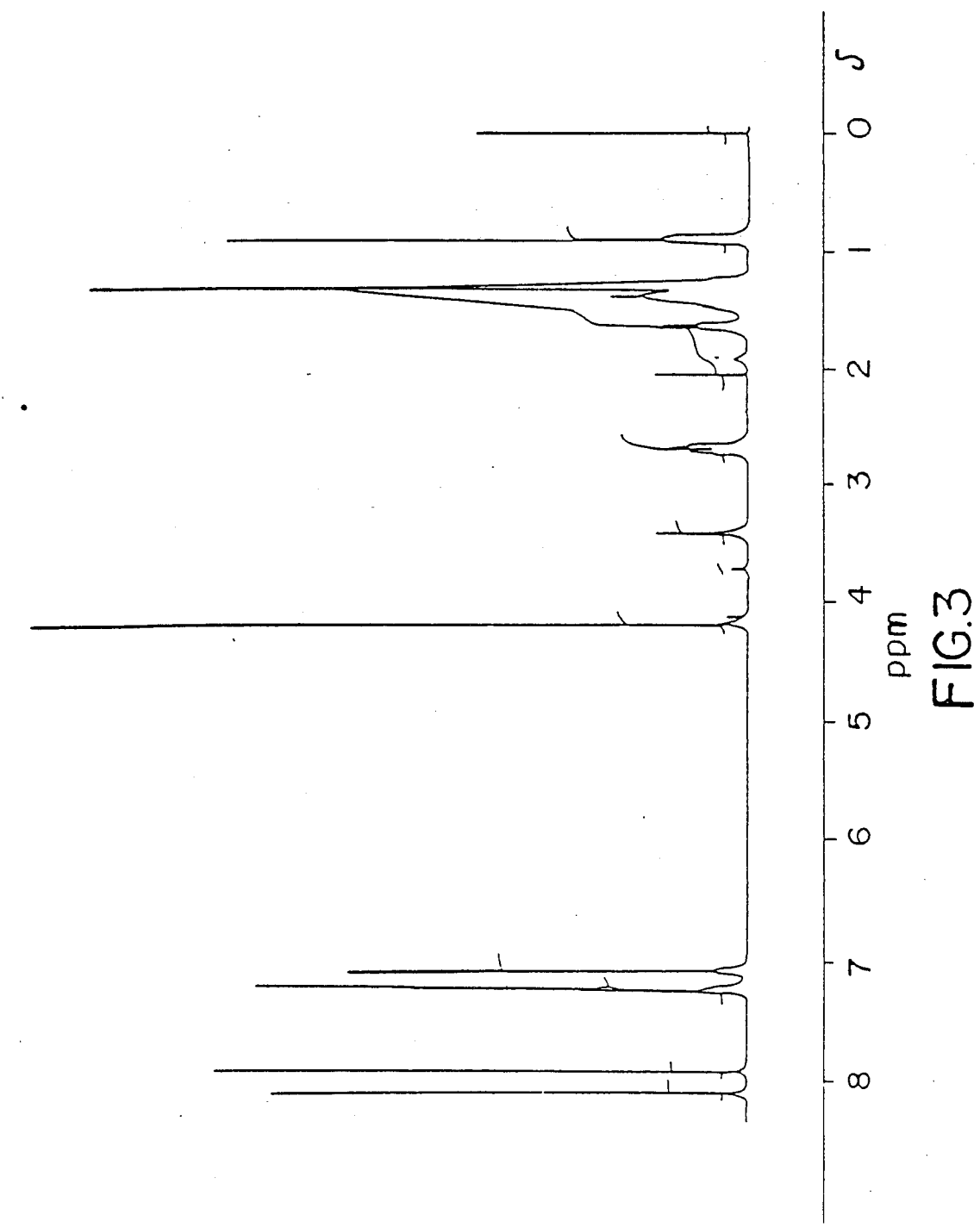
FIG. 3 represents the nuclear magnetic resonance spectrum characteristic of the compound prepared in Example 3.
Figure 4:
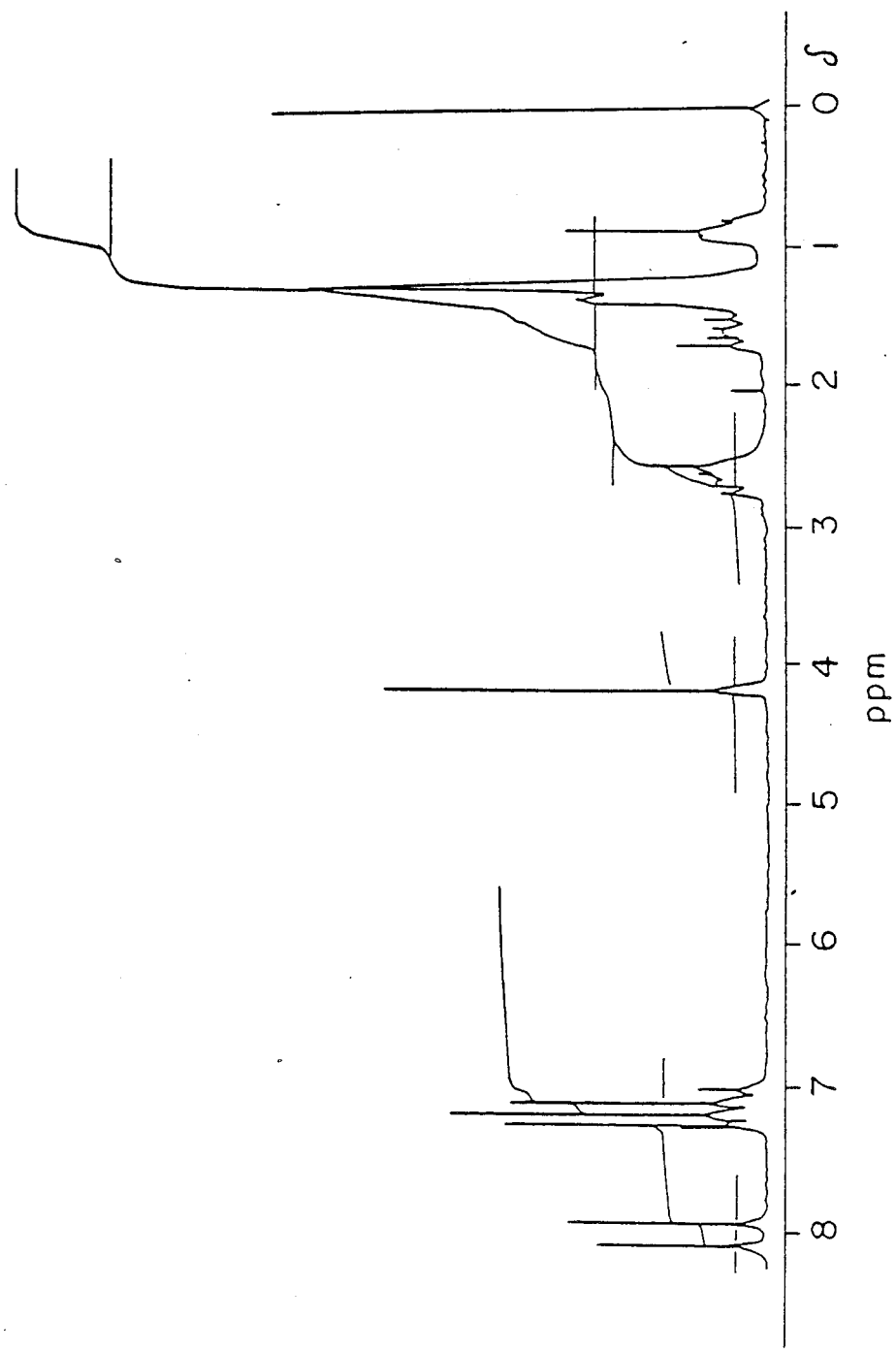
FIG. 4 represents the nuclear magnetic resonance spectrum characteristic of the compound prepared in Example 4.
Figure 5:
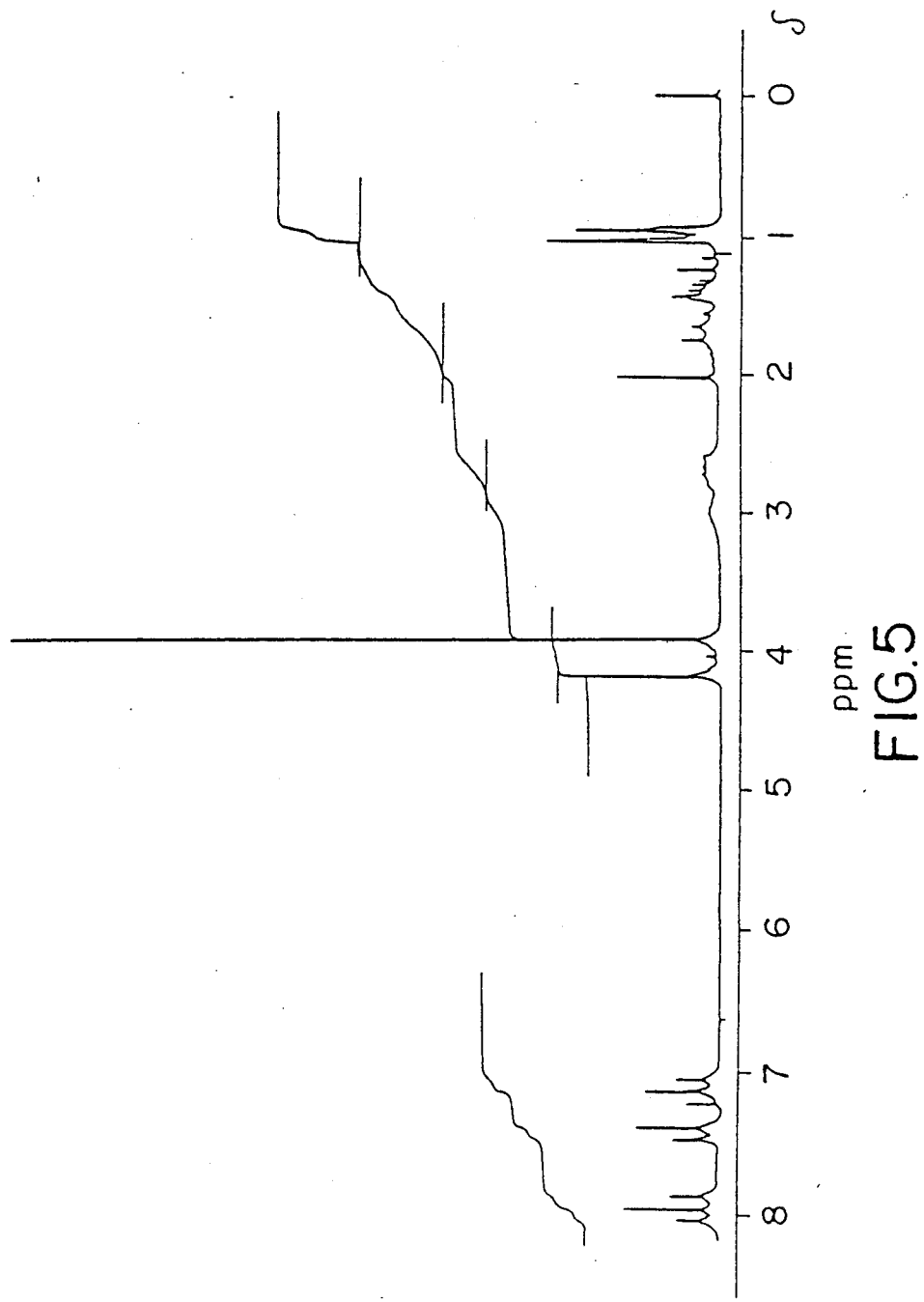
FIG. 5 represents the nuclear magnetic resonance spectrum characteristic of the compound prepared in Example 6.
Figure 6:
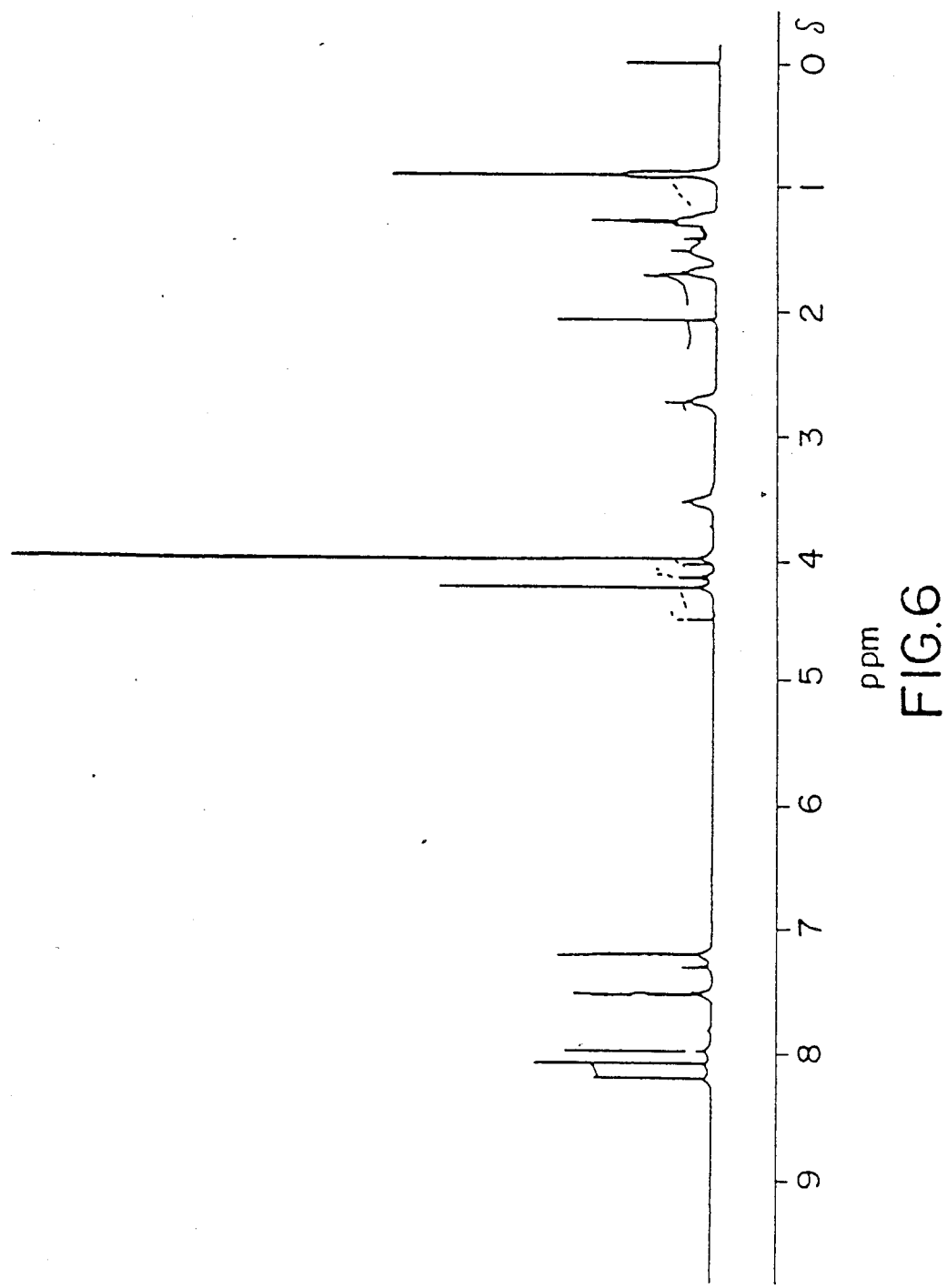
FIG. 6 represents the nuclear magnetic resonance spectrum characteristic of the compound prepared in Example 7.
Figure 7:
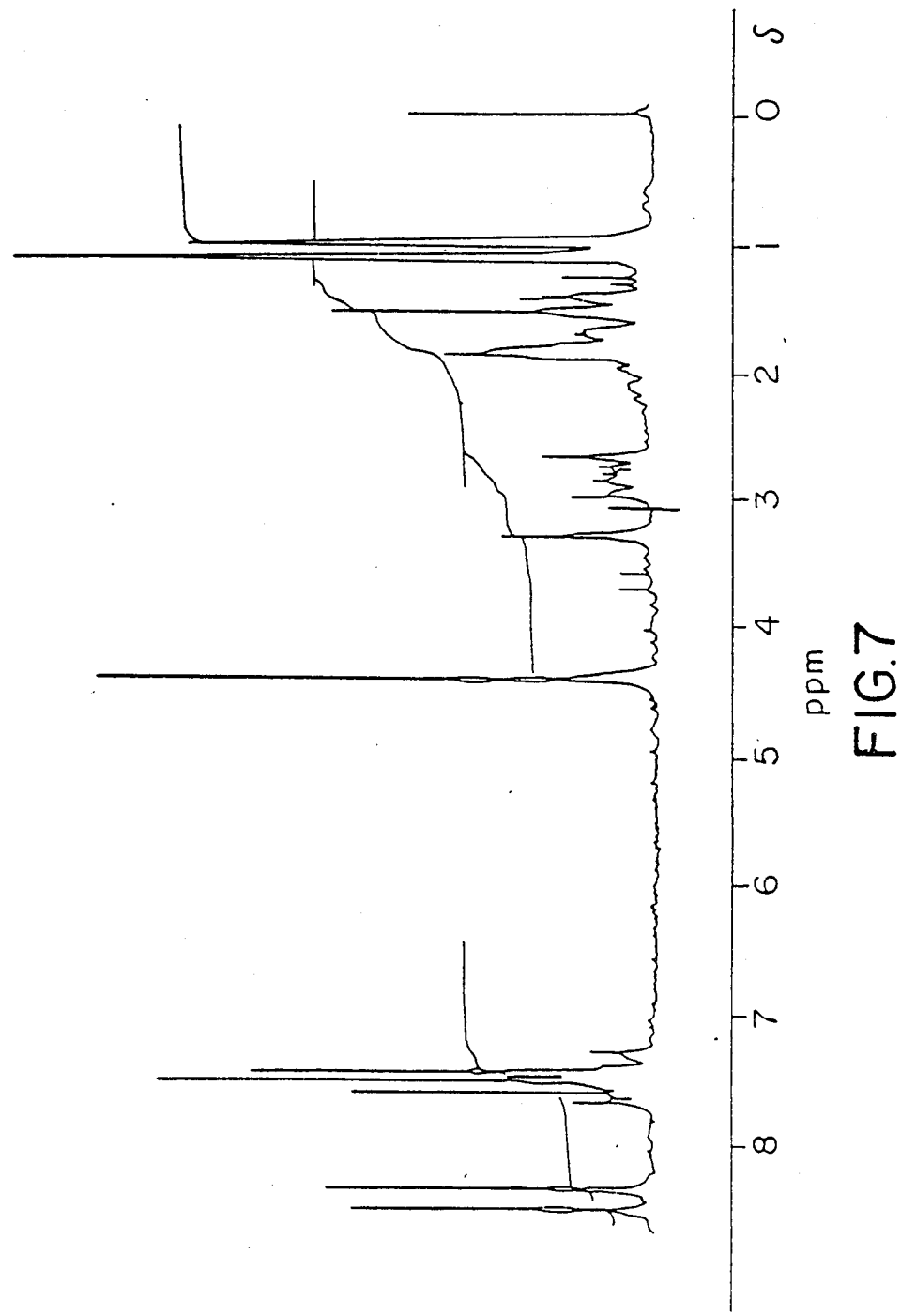
FIG. 7 represents the nuclear magnetic resonance spectrum characteristic of the compound prepared in Example 8.
Figure 8:
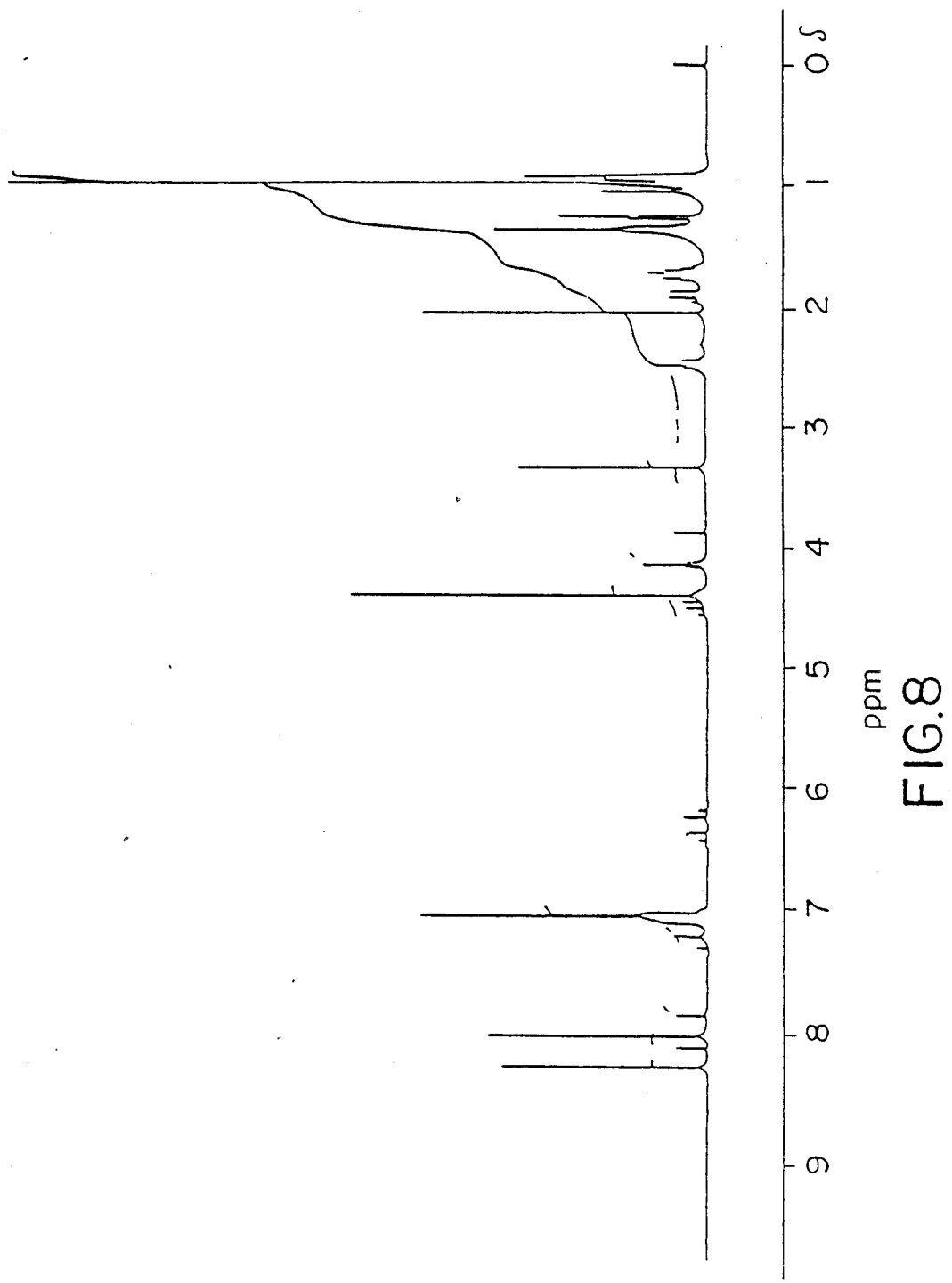
FIG. 8 represents the nuclear magnetic resonance spectrum characteristic of the compound prepared in Example 13.
Figure 9:
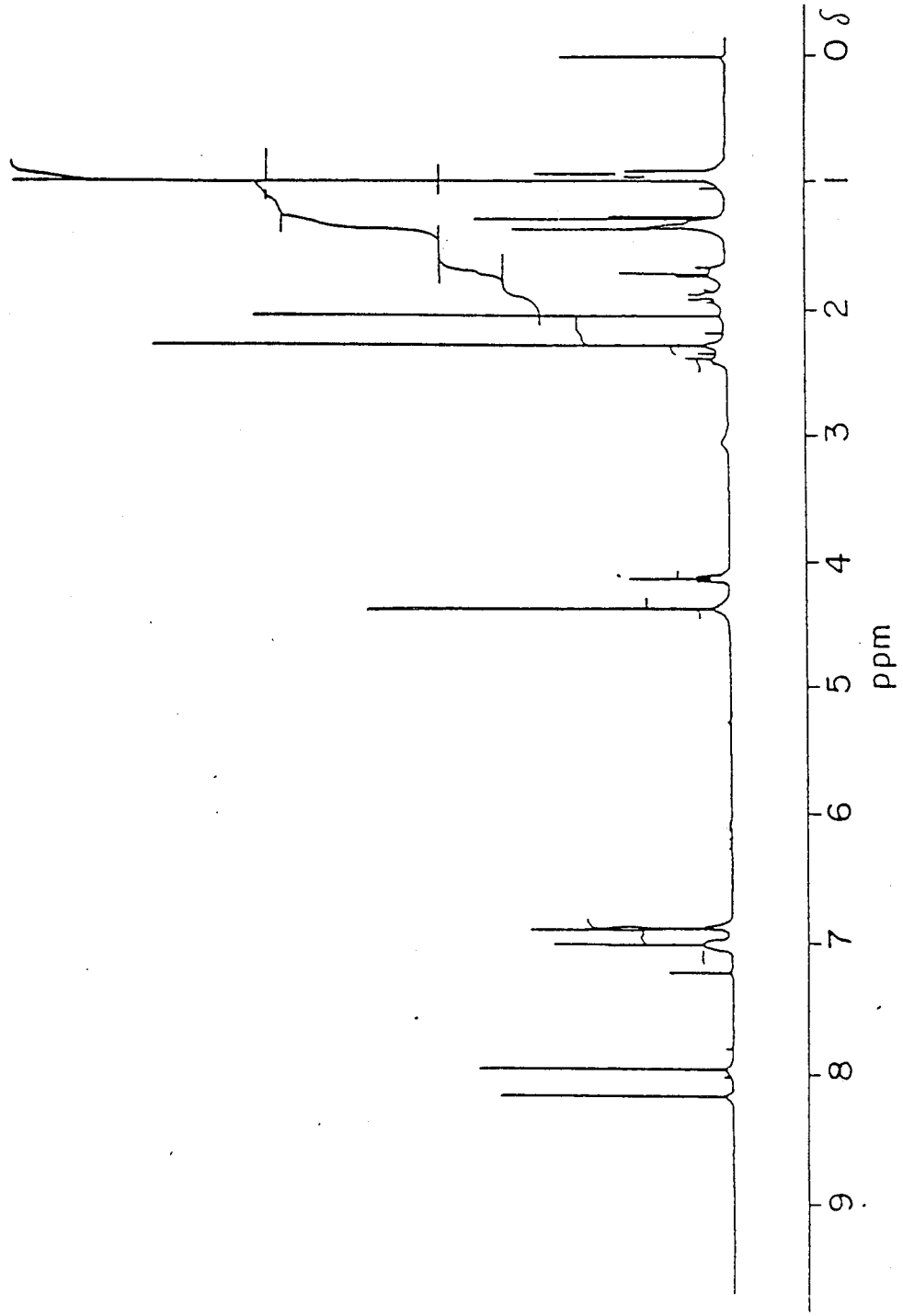
FIG. 9 represents the nuclear magnetic resonance spectrum characteristic of the compound prepared in Example 14.

The compound given below is employed as a comparison substance in the following use examples:

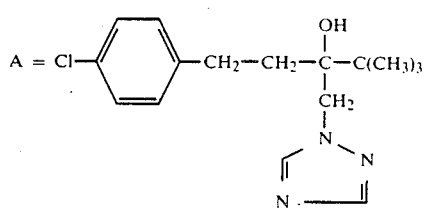

EXAMPLE A

Venturia test (apple)/curative

Solvent: 4.7 parts by weight of acetone
Emulsifier: 0.3 parts by weight of alkylaryl polyglycol ether To produce a suitable preparation of active compound, 1 part by weight of active compound is mixed with the stated amounts of solvent and emulsifier, and the concentrate is diluted with water to the desired concentration.

To test for curative activity, young plants are inoculated with an aqueous conidia suspension of the apple scab causative organism (*Venturia inaequalis*). The plants remain in an incubation cabin at 20° C. and 100% relative atmospheric humidity for 1 day and are then placed in a greenhouse. After a given number of hours, the plants are sprayed with the preparation of active compound until dripping wet.

The plants are then placed in a greenhouse at 20° C. and a relative atmospheric humidity of about 70%.

Evaluation is carried out 12 days after the inoculation.

The substances (I-1) and (I-7) according to the invention exhibit a better action than the comparative substance (A) in this test.

EXAMPLE B

Cercospora test (mungo bean)/protective

Solvent: 4.7 parts by weight of acetone
Emulsifier: 0.3 parts by weight of alkyl-aryl polyglycol ether To produce a suitable preparation of active compound, 1 part by weight of active compound is mixed with the stated amounts of solvent and emulsifier, and the concentrate is diluted with water to the desired concentration.

To test for protective activity, young plants are sprayed with the preparation of active compound until dripping wet. After the spray coating has dried, the plants are inoculated with an aqueous spore suspension of *Cercospora canescens* and remain in a dark incubation cabin at 22° C. and 100% relative atmospheric humidity for one day.

The plants are placed in an illuminated greenhouse at about 23° C. and a relative atmospheric humidity of about 80%.

Evaluation is carried out 20 days after the inoculation.

The substances (I-7) and (I-8) according to the invention exhibit a better activity than the comparative substance (A) in this test.

EXAMPLE C

Plant tolerance test

Test plant: cucumber
Duration of the test: 7 days
Solvent: 4.7 parts by weight of acetone
Emulsifier: 0.3 part by weight of alkyl-aryl polyglycol ether To produce a suitable preparation of active compound, 1 part by weight of active compound is mixed with the stated amounts of solvent and emulsifier, and the concentrate is diluted with water to the desired concentration.

Young plants are sprayed with this preparation of active compound until dripping wet and are placed in a greenhouse at about 20° C.

The plants are evaluated for damage, such as impairment of growth, discoloration and necrosis.

The compounds (I-1) and (I-7) according to the invention exhibit a better tolerance than the comparative substance (A) in this test.

EXAMPLE D

Erysiphe test (barley)/seed treatment

The active compounds are used as dry dressings. These are prepared by extending the particular active compound with a ground mineral to give a finely pulverulent mixture, which ensures uniform distribution on the seed surface.

To apply the dressing, the seed is shaken with the dressing in a closed glass flask for 3 minutes.

3 batches of 12 grains of the barley are sown 2 cm deep in standard soil. 7 days after sowing, when the young plants have unfolded their first leaf, they are dusted with spores of *Erysiphe graminis* f. sp. hordei.

The plants are placed in a greenhouse at a temperature of about 20° C. and a relative atmospheric humidity of about 80% in order to promote the development of mildew pustules.

Evaluation is carried out 7 days after the inoculation.

The compound (I-8) according to the invention exhibits a better action than the comparative substance (A) in this test.

It is understood that the specification and examples are illustrative but not limitative of the present invention and that other embodiments within the spirit and scope of the invention will suggest themselves to those skilled in the art.

We claim:

1. An oxirane of the formula

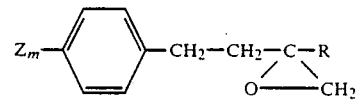

in which
R represents a radical of the formula —CH$_2$—CH(CH$_3$)$_2$, —(CH$_2$)$_4$—CH$_3$, —(CH$_2$)$_5$—CH$_3$, —(CH$_2$)$_6$—CH$_3$,

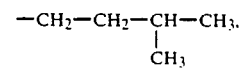

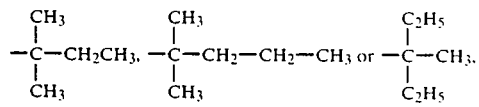

Z represents fluorine, chlorine, methyl, trifluoromethoxy or methoximinomethyl, and
m represents 0 or 1.

2. A compound according to claim 1, wherein such compound is 2-(4-chloro-phenylethyl)-2-(1,1-dimethylbutyl)-oxirane of the formula

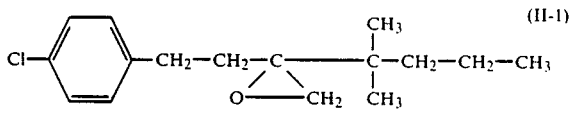

(II-1)

* * * * *